United States Patent
Lee et al.

(10) Patent No.: US 10,228,785 B2
(45) Date of Patent: *Mar. 12, 2019

(54) ULTRASOUND DIAGNOSIS APPARATUS AND METHOD AND COMPUTER-READABLE STORAGE MEDIUM

(71) Applicant: SAMSUNG ELECTRONICS CO., LTD., Suwon-si (KR)

(72) Inventors: Myong-woo Lee, Suwon-si (KR); Jong-geun Park, Seoul (KR); Ki-won Sohn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,827

(22) Filed: Nov. 20, 2017

(65) Prior Publication Data

US 2018/0088694 A1   Mar. 29, 2018

Related U.S. Application Data

(63) Continuation of application No. 14/637,560, filed on Mar. 4, 2015, now Pat. No. 9,841,831.

(30) Foreign Application Priority Data

Sep. 19, 2014 (KR) .......... 10-2014-0125300

(51) Int. Cl.
  *G09G 5/00* (2006.01)
  *G06F 3/041* (2006.01)
  (Continued)

(52) U.S. Cl.
  CPC .......... *G06F 3/041* (2013.01); *G06F 3/04845* (2013.01); *G06F 3/04883* (2013.01);
  (Continued)

(58) Field of Classification Search
  CPC .............. G06F 3/04845; G06F 3/0416; G06F 3/03547; G06F 19/30; G06F 19/3406; G06T 2207/10132; G06T 2207/20101
  USPC .......................................... 345/173; 715/863
  See application file for complete search history.

(56) References Cited

U.S. PATENT DOCUMENTS 5,984,870 A    11/1999 Giger et al.
9,841,831 B2 * 12/2017 Lee .......................... G06F 3/041
(Continued)

FOREIGN PATENT DOCUMENTS

JP    2012-19824 A    2/2012
JP    201497127 A     5/2014
(Continued)

OTHER PUBLICATIONS

Communication dated Nov. 27, 2015, issued by the Korean Intellectual Property Office in counterpart Korean Application No. 10-2014-0125300.

*Primary Examiner* — Jennifer T Nguyen
(74) *Attorney, Agent, or Firm* — Sughrue Mion, PLLC

(57) ABSTRACT

An ultrasound diagnostic apparatus includes a touch interface configured to display a screen comprising an ultrasound image of an object, and receive a user touch on the ultrasound image; and a controller configured to acquire a seed point, at which the user touch is sensed, acquire shape information of the object, and perform a control to display, on the ultrasound image, a touch point corresponding to the user touch, the touch point being determined based on the seed point and the shape information.

20 Claims, 11 Drawing Sheets

(51) Int. Cl.
  *G16H 40/63* (2018.01)
  *G06F 3/0484* (2013.01)
  *G06F 19/00* (2018.01)
  *G06F 3/0488* (2013.01)
  *G06T 7/12* (2017.01)
  *A61B 8/00* (2006.01)

(52) U.S. Cl.
  CPC ............. *G06F 19/00* (2013.01); *G06F 19/30* (2013.01); *G06T 7/12* (2017.01); *G16H 40/63* (2018.01); *A61B 8/467* (2013.01); *G06T 2207/10132* (2013.01); *G06T 2207/20101* (2013.01)

(56) References Cited

U.S. PATENT DOCUMENTS

| | | |
|---|---|---|
| 2003/0174890 A1 | 9/2003 | Yamauchi |
| 2004/0022447 A1 | 2/2004 | Mukhopadhyay et al. |
| 2008/0094356 A1* | 4/2008 | Ording ................ G06F 3/04812 345/157 |
| 2009/0226058 A1* | 9/2009 | Li ............................ G06T 7/11 382/128 |
| 2011/0231796 A1* | 9/2011 | Vigil .................... G06F 3/04883 715/810 |
| 2013/0072795 A1 | 3/2013 | Mo et al. |
| 2013/0147771 A1* | 6/2013 | Chuang ................. G06F 3/0488 345/178 |
| 2013/0343626 A1 | 12/2013 | Rico et al. |
| 2016/0188178 A1* | 6/2016 | Wang .................... G06F 3/0482 715/845 |
| 2017/0090675 A1* | 3/2017 | Lee ........................ A61B 8/465 |

FOREIGN PATENT DOCUMENTS

| | | |
|---|---|---|
| KR | 20030074414 A | 9/2003 |
| KR | 100644636 B1 | 11/2006 |
| KR | 101113218 B1 | 2/2012 |

* cited by examiner

ULTRASOUND DIAGNOSIS APPARATUS AND METHOD AND COMPUTER-READABLE STORAGE MEDIUM

CROSS-REFERENCE TO RELATED APPLICATION

This is a continuation application of U.S. application Ser. No. 14/637,560 filed Mar. 4, 2015, which claims priority from Korean Patent Application No. 10-2014-0125300, filed on Sep. 19, 2014, in the Korean Intellectual Property Office, the disclosure of which is incorporated herein in its entirety by reference.

BACKGROUND

1. Field

Apparatuses and methods consistent with exemplary embodiments relate to apparatuses and methods for ultrasound medical imaging, and more particularly, to providing an accurate touch-based operation on a user interface.

2. Description of the Related Art

Mobile devices, such as a smart phone or a tablet personal computer (PC), which has recently emerged, provide a touch-based user interface, and thus may be operated without a separate input device such as a mouse or a track ball. Due to convenience, the touch-based user interface is widely used in medical ultrasound imaging equipment.

An ultrasound diagnostic apparatus transmits ultrasound signals generated by transducers of a probe to an object and receives ultrasound echo signals reflected from the object, thereby obtaining images regarding the interior of the object (e.g., tomography of soft tissues or blood flow). In particular, an ultrasound diagnostic apparatus may be used for medical purposes including observation of the interior of an object, detection of foreign substances, and diagnosis of damage to the object. The ultrasound diagnostic apparatus may display information regarding an object in real time. Furthermore, unlike an X-ray apparatus, the ultrasound diagnostic apparatus does not involve any radioactive exposure, and thus is safe to use. Therefore, the ultrasound diagnostic apparatus is widely used together with different types of imaging diagnostic apparatuses such as computed tomography (CT) scanners, magnetic resonance imaging (MRI) apparatuses, and nuclear medicine diagnostic apparatuses.

When using the ultrasound imaging apparatus, a method that allows a user (e.g., a medical practitioner) needs to designate a measurement position of an object.

When a touch-based user interface is used, there is no need for a separate input device such as a mouse, and accordingly, no mouse cursor is displayed on a screen. The touch-based user interface may provide a button on the screen to be used by a user through a finger or a separate pen. However, a touch-based operation is less accurate than a mouse-based operation, which may be accurately controlled on a pixel-by-pixel basis. Thus, it may be difficult to input an accurate measurement point desired by the user using the touch-based user interface, when measuring a certain structure or organ using an ultrasound image.

SUMMARY

One or more exemplary embodiments provide apparatuses, methods, and non-transitory computer-readable storage media, which may allow a user to input an accurate point desired by the user, by using a touch-based user interface.

Additional aspects will be set forth in part in the description which follows and, in part, will be apparent from the description, or may be learned by practice of the exemplary embodiments.

According to one or more exemplary embodiments, an ultrasound diagnostic apparatus includes: a touch interface displaying a screen including an ultrasound image, and receiving a user touch on the ultrasound image; and a controller acquiring a point, at which the user touch is sensed, as a seed point, acquiring shape information of an object included in the ultrasound image, and performing control to display a touch point corresponding to the user touch on the ultrasound image, based on the seed point and the shape information.

The controller may acquire the touch point, based on a distance between the seed point and a predetermined point of the object included in the shape information and perform control to display the touch point on the ultrasound image.

The controller may acquire the shape information including an edge of the object, based on the ultrasound image, acquire distances between the seed point and points on the edge, and acquire the touch point, based on the distances between the seed point and the points on the edge.

The controller may acquire a region of interest (ROI) having a predetermined size on the ultrasound image, based on the seed point and acquire the shape information of the object by image processing the ROI.

The touch interface may display an image of the ROI on the ultrasound image.

When the touch interface receives a seed line including seed points from a user, the controller may acquire a user touch line in real time, based on the seed line.

The shape information of the object may include an edge of the object, and the controller may automatically acquire a point, which is closest to the seed point among points on the edge, as the touch point.

The controller may acquire one or more candidate touch points, which are within a predetermined distance from the seed point, among points on the shape information of the object.

The touch interface may receive a predetermined motion pattern from a user, and the controller may acquire one of the one or more candidate touch points as the touch point, based on the received predetermined motion pattern.

The touch interface may display in real time a screen including at least one of the ultrasound image, the seed point, the touch point, and the shape information of the object.

When the touch interface receives a predetermined motion pattern from a user, the controller may acquire the seed point as the touch point.

The controller may acquire the shape information of the object by morphological image processing.

The morphological image processing may include at least one of an edge detection algorithm, an image segmentation algorithm, and a machine learning algorithm.

According to one or more exemplary embodiments, an ultrasound diagnostic method includes: receiving a user touch on an ultrasound image; acquiring a point, at which the user touch is sensed, as a seed point; acquiring shape information of an object included in the ultrasound image; acquiring a touch point corresponding to the user touch, based on the seed point and the shape information; and displaying the touch point together with the ultrasound image.

The acquiring of the touch point may include acquiring the touch point, based on a distance between the seed point and a predetermined point of the object included in the shape information.

The acquiring of the shape information of the object may include acquiring the shape information including an edge of the object, based on the ultrasound image, and the acquiring of the touch point may include: acquiring distances between the seed point and points on the edge; and acquiring the touch point, based on the distances between the seed point and the points on the edge.

The acquiring of the shape information of the object may include: acquiring a region of interest (ROI) having a predetermined size on the ultrasound image, based on the seed point; and acquiring the shape information of the object by image processing the ROI.

The displaying of the touch point may include displaying an enlarged screen of the ROI on the ultrasound image.

The acquiring of the seed point may include receiving a seed line including seed points from a user, and the acquiring of the touch point may include acquiring a touch line corresponding to the user touch in real time, based on the seed line.

The shape information of the object may include an edge of the object, and the acquiring of the touch point may include automatically acquiring a point, which is closest to the seed point among points on the edge, as the touch point.

The acquiring of the touch point may include acquiring one or more candidate touch points, which are within a predetermined distance from the seed point, among points on the shape information of the object.

The receiving of the user touch may include receiving a predetermined motion pattern from a user, and the acquiring of the touch point may include acquiring one of the one or more candidate touch points as the touch point, based on the received predetermined motion pattern.

The displaying of the touch point may include displaying in real time a screen including at least one of the ultrasound image, the seed point, the touch point, and the shape information of the object.

The receiving of the user touch may include receiving a predetermined motion pattern from a user, and the acquiring of the touch point may include acquiring the seed point as the touch point.

The acquiring of the shape information of the object may include acquiring the shape information of the object by morphological image processing.

The morphological image processing may include at least one of an edge detection algorithm, an image segmentation algorithm, and a machine learning algorithm.

According to one or more exemplary embodiments, a non-transitory computer-readable recording medium stores a program that performs the above ultrasound diagnostic method when executed by a computer.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
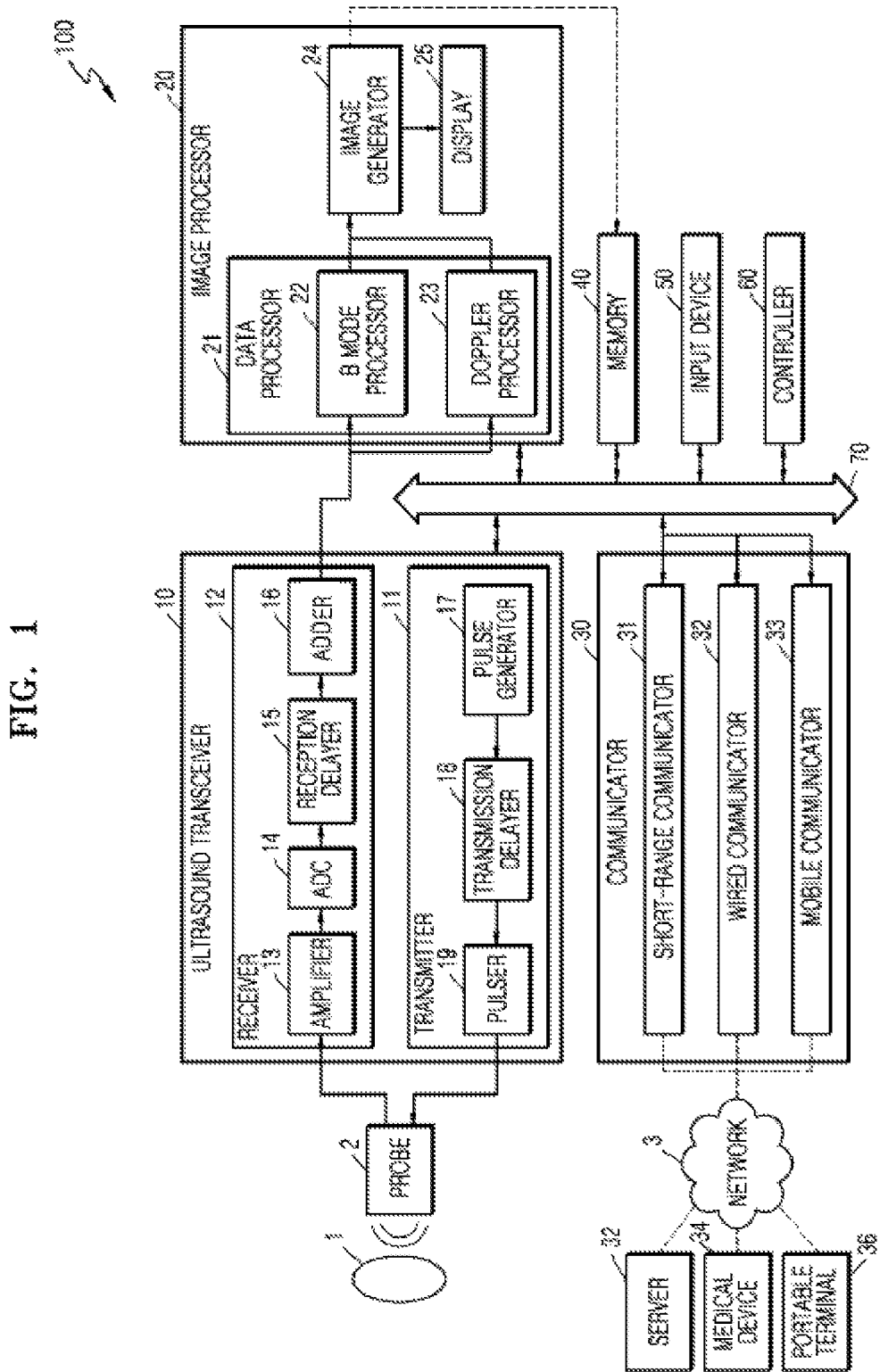
FIG. 1 is a diagram illustrating an ultrasound imaging apparatus according to an exemplary embodiment.

Certain exemplary embodiments are described in greater detail below with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the disclosure. As used herein, expressions such as "at least one of," when preceding a list of elements, modify the entire list of elements and do not modify the individual elements of the list.

When something "comprises" or "includes" a component, another component may be further included unless specified otherwise. Also, the terms "unit" and "module" used herein represent a unit for processing at least one function or operation, which may be implemented by hardware, software, or a combination of hardware and software.

Throughout the specification, an "ultrasound image" refers to an image of an object acquired by using an ultrasonic wave. Also, an "object" may include a person or an animal, or a part of a person or an animal. For example, the object may include an organ such as a liver, a heart, a womb, a brain, a breast, or an abdomen, or a blood vessel. Also, the object may include a phantom. The phantom may refer to a material having a volume that is approximately the intensity and effective atomic number of a living thing, and may include a spherical phantom having a property similar to a human body.

Also, a "user" may be, but is not limited to, a medical expert such as a doctor, a nurse, a medical laboratory technologist, a medial image expert, or a technician who repairs a medical apparatus.

Also, a "touch" may include not only a touch to an ultrasound image by the user but also a proximity touch to an ultrasound image so that an ultrasound diagnostic apparatus may recognize a user input. Also, the "touch" may include not only a touch to an ultrasound image by a body part of the user but also, for example, a touch to an ultrasound image by an object such as a touch pen or a rod.

Hereinafter, exemplary embodiments will be described in detail with reference to the accompanying drawings.

FIG. 1 is a diagram illustrating an ultrasound imaging apparatus according to an exemplary embodiment.

FIG. 1 illustrates an overall configuration of an ultrasound diagnostic apparatus 100 according to an exemplary embodiment.

Referring to FIG. 1, the ultrasound diagnostic apparatus 100 may include a probe 2, an ultrasound transceiver 10, an image processor 20, a communicator 30, a memory 40, an input device 50, and a controller 60. The components stated above may be connected to one another via buses 70.

The ultrasound diagnostic apparatus 100 may be embodied not only as a cart type apparatus, but also as a portable apparatus. Examples of portable ultrasound diagnostic apparatuses may include a picture archiving and communication system (PACS) viewer, a smart phone, a laptop computer, a personal digital assistant (PDA), and a tablet personal computer (PC); however, the exemplary embodiments are not limited thereto.

The probe 2 transmits an ultrasound signal to an object 1 according to a driving signal applied from the ultrasound transceiver 10 and receives an echo signal reflected from the object 1. The probe 2 includes a plurality of transducers, and the plurality of transducers oscillate according to an electrical signal transmitted thereto and generate an ultrasound wave, that is, acoustic energy. Also, the probe 2 may be connected to a main body of the ultrasound diagnostic apparatus 100 by wire or wirelessly. According to exemplary embodiments, the ultrasound diagnostic apparatus 100 may include a plurality of probes 2.

A transmitter 11 supplies a driving signal to the probe 2 and includes a pulse generator 17, a transmission delayer 18, and a pulser 19. The pulse generator 17 generates pulses for forming transmission ultrasound waves according to a predetermined pulse repetition frequency (PRF), and the transmission delayer 18 applies a delay time for determining transmission directionality to the pulses. The pulses to which a delay time is applied correspond to a plurality of piezoelectric vibrators included in the probe 2, respectively. The pulser 19 applies a driving signal (or a driving pulse) to the probe 2 at a timing corresponding to each pulse to which a delay time is applied.

A receiver 12 generates ultrasound data by processing echo signals received from the probe 2 and may include an amplifier 13, an analog-digital converter (ADC) 14, a reception delayer 15, and a adder 16. The amplifier 13 amplifies echo signals in each channel, and the ADC 14 analog-to-digital converts the amplified echo signals. The reception delayer 15 applies delay times for determining reception directionality to the digital-converted echo signals, and the adder 16 generates ultrasound data by summing the echo signals processed by the reception delayer 15. Also, according to exemplary embodiments, the amplifier 13 may be omitted from the receiver 12. In other words, when the sensitivity of the probe 2 or the capability to process bits by the ADC 14 is enhanced, the amplifier 13 may be omitted.

The image processor 20 generates an ultrasound image by scan-converting ultrasound data generated by the ultrasound transceiver 10 and displays the ultrasound image. The ultrasound image may include not only a gray-scale image obtained by scanning the object 1 in, for example, an amplitude (A) mode, a brightness (B) mode, and/or a motion (M) mode, but also a Doppler image representing a motion of the object 1 by using a Doppler effect. The Doppler image may include a bloodstream Doppler image (also referred to as a color Doppler image) representing a flow of blood, a tissue Doppler image representing a motion of a tissue, and a spectral Doppler image representing a movement speed of the object 1 in a waveform.

A B mode processor 22 extracts B mode components from ultrasound data and processes the B mode components. An image generator 24 may generate an ultrasound image representing signal intensities as brightness, based on the B mode components extracted by the B mode processor 22.

A Doppler processor 23 may extract Doppler components from the ultrasound data, and the image generator 24 may generate a Doppler image representing a motion of the object 1 as colors or waveforms based on the extracted Doppler components.

The image generator 24 according to an exemplary embodiment may generate a three-dimensional (3D) ultrasound image through volume-rendering of volume data and may also generate an elasticity image that visualizes the deformation of the object 1 due to a pressure. In addition, the image generator 24 may display various additional information in an ultrasound image by using texts and graphics. The generated ultrasound image may be stored in the memory 40.

A display 25 displays the generated ultrasound image. The display 25 may display not only an ultrasound image, but also various information processed by the ultrasound diagnostic apparatus 100 on a screen via a graphic user interface (GUI). The ultrasound diagnostic apparatus 100 may include two or more displays 25 according to exemplary embodiments.

The communicator 30 is connected by wire or wirelessly to a network 3 to communicate with an external device or a server (e.g., a server 32). The communicator 30 may exchange data with, for example, a hospital server or other medical apparatuses in a hospital connected through a picture archiving and communication System (PACS). Also, the communicator 30 may perform data communication according to the digital imaging and communications in medicine (DICOM) standard.

The communicator 30 may transmit and receive data related to diagnosis of the object 1, e.g., an ultrasound image, ultrasound data, and/or Doppler data of the object 1, via the network 3 and may also transmit and receive medical images obtained by other medical apparatuses, e.g., a computed tomography (CT) image, a magnetic resonance (MR) image, and/or an X-ray image. In addition, the communicator 30 may receive information related to a diagnosis history or a treatment schedule of a patient from a server and use the information to diagnose the object 1. In addition, the communicator 30 may perform data communication not only with a server or a medical apparatus in a hospital, but also with a portable terminal of a user, e.g., a doctor or a patient.

The communicator 30 may be connected by wire or wirelessly to the network 3 to exchange data with the server 32, a medical device 34, or a portable terminal 36. The communicator 30 may include one or more components that enable communication with external devices, and may include, for example, a short-range communicator 31, a wired communicator 32, and a mobile communicator 33.

The short-range communicator 31 performs short-range communication within a predetermined distance. Examples of short-range communication techniques according to an exemplary embodiment may include wireless local area network (LAN), Wi-Fi, Bluetooth, Zigbee, Wi-Fi Direct (WFD), ultra wideband (UWB), infrared data association (IrDA), Bluetooth low energy (BLE), and near field communication (NFC); however, the exemplary embodiments are not limited thereto.

The wired communicator 32 performs communication using electrical signals or optical signals. Examples of wired communication techniques according to an exemplary embodiment may include a twisted pair cable, a coaxial cable, an optical fiber cable, and an Ethernet cable.

The mobile communicator 33 transmits and receives wireless signals to and from at least one of a base station, an external terminal, and a server on a mobile communication network. Herein, the wireless signals may include, for example, voice call signals, video call signals, or various types of data for transmission and reception of text and/or multimedia messages.

The memory 40 stores various data processed by the ultrasound diagnostic apparatus 100. For example, the memory 40 may store medical data related to diagnosis of the object 1, such as ultrasound data and ultrasound images that are input or output and may also store algorithms or programs to be executed in the ultrasound diagnostic apparatus 100.

The memory 40 may be embodied as any of various storage media such as a flash memory, a hard disk drive, and an electrically erasable programmable read-only memory (EEPROM). Also, the ultrasound diagnostic apparatus 100 may utilize web storage or a cloud server that functions as the memory 40 online.

The input device 50 refers to a device via which a user inputs data for controlling the ultrasound diagnostic apparatus 100. The input device 50 may include hardware components, such as a keypad, a mouse, a touch panel, a touch screen, a track ball, and a jog switch. However, the exemplary embodiments are not limited thereto, and the input device 50 may further include various different input units, such as an electrocardiogram measurer, a respiration measurer, a voice recognition sensor, a gesture recognition sensor, a fingerprint recognition sensor, an iris recognition sensor, a depth sensor, and a distance sensor.

The controller 60 may control overall operations of the ultrasonic diagnostic apparatus 100. In other words, the controller 60 may control operations among the probe 2, the ultrasound transceiver 10, the image processor 20, the communicator 30, the memory 40, and the input device 50 illustrated in FIG. 1.

All or some of the probe 2, the ultrasound transceiver 10, the image processor 20, the communicator 30, the memory 40, the input device 50, and the controller 60 may be operated by software modules. However, the exemplary embodiments are not limited thereto, and some of the above components may be operated by hardware modules. Also, at least one of the ultrasound transceiver 10, the image processor 20, and the communicator 30 may be included in the controller 60; however, the exemplary embodiments are not limited thereto.

For diagnosis of a disease by using an ultrasound image, a marker may be set to indicate a predetermined position or set a diagnosis region in an ultrasound image including an object.

In detail, the marker may be set at a portion that is to be observed in detail by the user to diagnose a disease or to check the condition of a patient. The exemplary embodiments provide an ultrasound diagnostic apparatus and an ultrasound image display method, which may control the display of an ultrasound image to more accurately diagnose an object region in which the marker is set.

Figure 2:
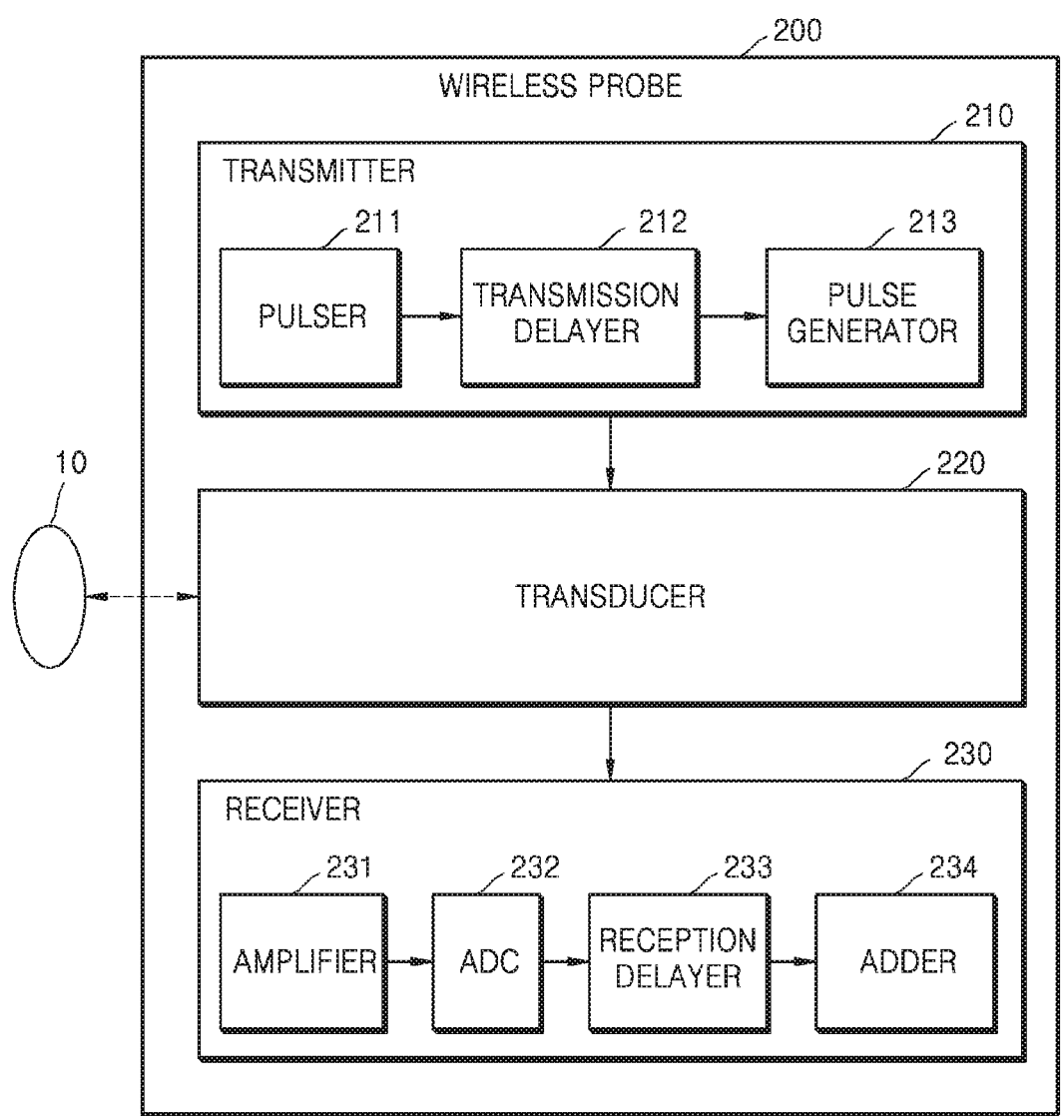
FIG. 2 is a block diagram illustrating a configuration of a wireless probe according to an exemplary embodiment.

FIG. 2 is a block diagram illustrating a configuration of a wireless probe 200 according to an exemplary embodiment.

The wireless probe 200 may include a plurality of transducers as described with reference to FIG. 1, and may include some or all of the configurations of the ultrasound transceiver 10 of FIG. 1 according to exemplary embodiments.

The wireless probe 200 according to an exemplary embodiment illustrated in FIG. 2 may include a transmitter 210, a transducer 220, and a receiver 230. The transmitter 210, the transducer 220, and the receiver 230 are similar to the respective corresponding components described with reference to FIG. 1, and thus, detailed descriptions thereof will be omitted. The wireless probe 200 may selectively include a reception delayer 233 and a adder 234 according to exemplary embodiments.

The wireless probe 200 may transmit an ultrasound signal to the object 1 and receive an echo signal therefrom, and may generate ultrasound data and wirelessly transmit the ultrasound data to the ultrasound diagnostic apparatus 100 of FIG. 1.

The input device 50 having a touch-based user interface may be less accurate than a mouse-based operation, which is controlled on a pixel-by-pixel basis. Thus, it may be difficult to input an accurate point desired by the user by using the touch-based user interface, when measuring a certain structure or organ using an ultrasound image.

One or more exemplary embodiments may enable the user to accurately and conveniently input a measurement point. Hereinafter, ultrasound diagnostic apparatuses and methods and computer-readable storage media therefor according to one or more exemplary embodiments will be described in detail with reference to FIGS. 3 to 13.

An ultrasound diagnostic apparatus may acquire a signal from a probe, generate an ultrasound image, and measure the length, angle, area, or volume of a certain organ or structure on the ultrasound image. Based on the measurement, the ultrasound diagnostic apparatus may acquire information about the object, for example, an abnormal region in a body or may acquire information about a gestational age or the like. Since the ultrasound diagnostic apparatus is widely used for medical diagnosis, the ultrasound diagnosis needs to have accuracy as well as usability.

Mobile equipment, such as a smart phone or a tablet PC provides a touch-based user interface, and thus may be operated without a separate input device such as a mouse or a track ball. Due to convenience, the touch-based user interface has become widely used in medical ultrasound imaging equipment. Therefore, it is needed to increase the accuracy of a touch point when the touch-based user interface is used in the ultrasound diagnostic apparatus.

Figure 3:
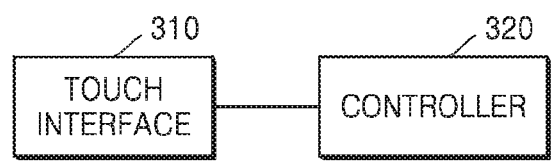
FIG. 3 is a diagram illustrating an ultrasound diagnostic apparatus according to an exemplary embodiment.

FIG. 3 is a diagram illustrating an ultrasound diagnostic apparatus according to an exemplary embodiment.

The ultrasound diagnostic apparatus according to an exemplary embodiment may include a touch interface 310 and a controller 320. Since a touch interface 310 and a controller 320 illustrated in FIG. 3 respectively correspond to the input device 50 and the controller 60 illustrated in FIG. 1, redundant descriptions thereof will be omitted herein.

The touch interface 310 displays a screen including an ultrasound image, and receives a user touch on the ultrasound image. The controller 320 acquires a point, at which the user touch is sensed, as a seed point, acquires shape information of an object included in the ultrasound image, and performs control to display a touch point corresponding to the user touch on the ultrasound image, based on the seed point and the shape information.

Also, the controller 320 acquires the touch point, based on a distance between the seed point and a predetermined point of the object included in the shape information, and performs control to display the touch point in the ultrasound image.

Also, the controller 320 acquires the shape information including an edge of the object, based on the ultrasound image, acquires distances between the seed point and points on the edge, and acquires the touch point, based on the distances between the seed point and the points on the edge.

The touch interface 310 receives an input from a user. Also, the touch interface 310 may be the input device 50 of FIG. 1. The touch interface 310 is a touch-based user interface. That is, the touch interface 310 may recognize a user touch and receive an input from the user. In detail, the touch interface 310 generates and displays a user interface screen for receiving an input of a predetermined command or data from the user, and receives an input of a predetermined command or data from the user through the user interface screen. For example, the touch interface 310 may be formed to include a touch screen. Herein, the touch screen includes a touch pad (not illustrated) connected with a display panel (not illustrated), and displays the user interface screen on the display panel. When a predetermined command is input through the user interface screen, the touch pad may sense and recognize the predetermined command input by the user.

For example, when the touch interface 310 displays an ultrasound image, the user may input a point to be measured, by touching a point on the ultrasound image while viewing the ultrasound image through the touch interface 310. The touch interface 310 may be a pressure-sensitive user interface, an electrostatic user interface, or an infrared user interface. However, the touch interface 310 may be any touch-based user interface and is not limited to a pressure-sensitive user interface, an electrostatic user interface, and an infrared user interface.

The seed point refers to a point received from the user. For example, when the user touches a point to be measured on the ultrasound image with a finger or a touch pen, the touch interface 310 may sense and recognize the point touched by the user as the seed point. The seed point may be acquired as position information including a Cartesian coordinate value or a polar coordinate value with respect to the ultrasound image.

There may be cases where a difference exists between the seed point and a point intended by the user. For example, when the user touches his finger on the touch interface 310, a contact surface area between the touch interface 310 and the finger of the user is relatively large. Therefore, while the touch interface 310 acquires a predetermined point of the contact surface area as the seed point, the seed point may be different from the point intended by the user. Also, due to an error in the touch interface 310, there may be a difference between the seed point and the point intended by the user. According to an exemplary embodiment, the point intended by the user may be more accurately acquired as the touch point, based on the seed point.

The shape information of the object is information about the shape of the object that may be obtained by image processing the ultrasound image of the object. When the shape information of the object is used, the size, shape, position, and angle of the object may be more easily detected and thus the ultrasound image of the object may be more easily processed. The shape information of the object may be, for example, edge information of the object.

The touch point refers to a point that is intended to be touched by the user. As described above, the seed point may be different from the touch point intended by the user. According to an exemplary embodiment, the touch point intended by the user may be acquired based on the seed point that is actually received from the user.

Figure 4:
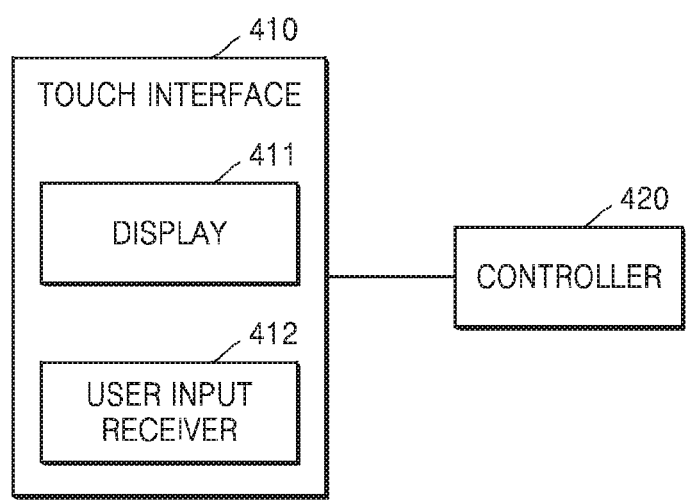
FIG. 4 is a diagram illustrating an ultrasound diagnostic apparatus according to an exemplary embodiment.

FIG. 4 is a diagram illustrating an ultrasound diagnostic apparatus according to another exemplary embodiment.

Referring to FIG. 4, the ultrasound diagnostic apparatus according to an exemplary embodiment may include a touch interface 410 and a controller 420. Since the touch interface 410 and the controller 420 illustrated in FIG. 4 respectively correspond to the touch interface 310 and the controller 320 illustrated in FIG. 3, redundant descriptions thereof will be omitted herein.

Also, the touch interface 410 may include a display 411 and a user input receiver 412. The display 411 may display various visual data acquired according to an exemplary embodiment. The display 411 may correspond to the display 25 of FIG. 1 and include a display panel. The display 411 may display in real time a screen including at least one of the ultrasound image, the seed point, the edge, and the touch point. Also, at least one of the ultrasound image, the seed point, the edge, and the touch point displayed on the display 411 may be converted into data to be stored in a computer-readable storage medium.

The user input receiver 412 receives an input from the user. In detail, the user input receiver 412 may include a touch panel attached to the display 411. The user input receiver 412 may use a pressure-sensitive user interface, an electrostatic user interface, or an infrared user interface. However, the user input receiver 412 may use any touch-based user interface and is not limited to a pressure-sensitive user interface, an electrostatic user interface, or an infrared user interface.

Figure 5:
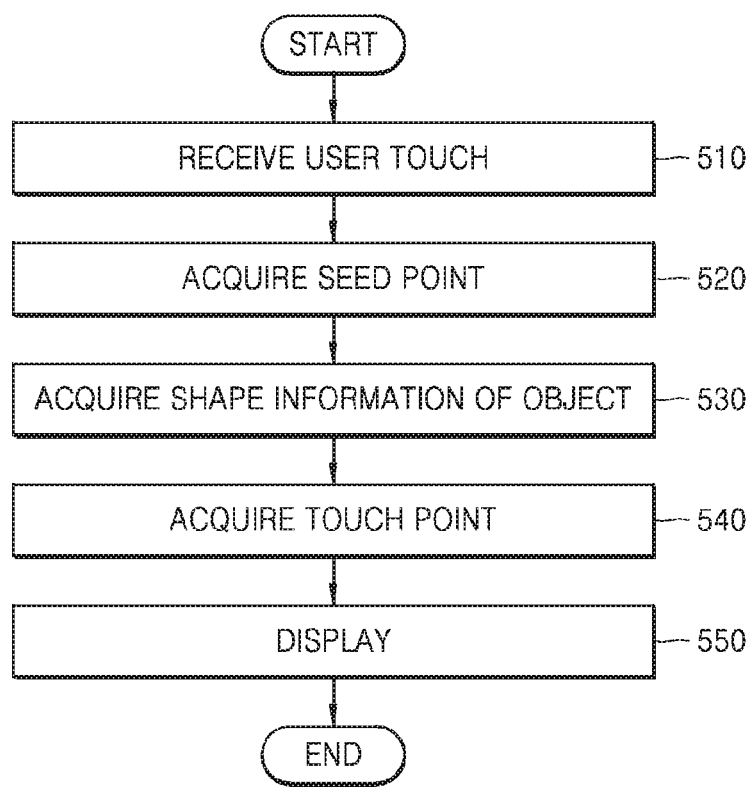
FIG. 5 is a flowchart illustrating an ultrasound diagnostic method according to an exemplary embodiment.

FIG. 5 is a diagram illustrating an ultrasound diagnostic method according to another exemplary embodiment.

Referring to FIG. 5, the ultrasound diagnostic method according to an exemplary embodiment may include an operation 510 of receiving a user touch, an operation 520 of acquiring a seed point, an operation 530 of acquiring shape information of an object, an operation 540 of acquiring a touch point, and an operation 550 of displaying the touch point. Since a portion of detailed description of FIG. 5 overlaps with the description of FIG. 3, redundant descriptions thereof will be omitted herein. The operation 510 of receiving the user touch is an operation of receiving a touch input from a user and may be performed by the user input receiver 412. The touch input from the user may be an action of touching the touch interface 310 using a finger. The operation 520 of acquiring the seed point is an operation of acquiring a seed point on an ultrasound image, based on the touch input received from the user. The operation 530 of acquiring the shape information of the object is an operation of image processing an ultrasound image of the object. By this operation, the size, shape, position, and angle of the object may be more easily detected. The operation 540 of acquiring the touch point is an operation of acquiring a touch point intended by the user, based on the shape information of the object. The operations 520, 530, and 540 may be performed by the controller 420. The displaying operation 550 is an operation of displaying the touch point intended by the user together with the ultrasound image. The displaying operation 550 may be performed by the display 411.

Also, the operation 530 of acquiring the shape information of the object may include an operation of acquiring the shape information including an edge of the object, based on the ultrasound image.

The operation 540 of acquiring the touch point may include an operation of acquiring the touch point, based on a distance between the seed point and a predetermined point of the object obtained based on the shape information. In detail, the operation 540 of acquiring the touch point may include an operation of acquiring distances between the seed point and points on the edge of the object, and an operation of acquiring the touch point, based on the distances between the seed point and the points on the edge. An operation of acquiring the touch point, based on the shape information including the edge, will be described in detail with reference to FIG. 6.

Also, the operation 530 of acquiring the shape information of the object may include an operation of acquiring a region of interest (ROI) having a predetermined size on the ultrasound image, based on the seed point, and an operation of acquiring the shape information of the object by image processing an image of the ROI. The displaying operation 550 may include an operation of displaying an enlarged image of the ROI on the ultrasound image.

Also, the operation 520 of acquiring the seed point may include an operation of receiving a seed line including seed points from the user. Also, the operation 540 of acquiring the touch point may include an operation of acquiring a touch line corresponding to the user touch in real time, based on the seed line.

The shape information of the object may include an edge of the object, and the operation 540 of acquiring the touch point may include an operation of automatically acquiring a point, which is closest to the seed point among points on the edge, as the touch point. The operation 540 of acquiring the touch point may include an operation of acquiring one or more candidate touch points, which are within a predetermined distance from the seed point, among points on the shape information of the object. The operation 510 of receiving the user touch may include an operation of receiving a predetermined motion pattern from the user. The operation 540 of acquiring the touch point may include an operation of acquiring one of the one or more candidate touch points as the touch point, based on the received predetermined motion pattern.

The displaying operation 550 may include an operation of displaying in real time a screen including at least one of the ultrasound image, the seed point, the touch point, and the shape information of the object. The operation 510 of receiving the user touch may include an operation of receiving a predetermined motion pattern from the user. Also, the operation 540 of acquiring the touch point may include an operation of acquiring the seed point as the touch point. The operation 530 of acquiring the shape information of the object may include an operation of acquiring the shape information of the object by performing morphological image processing on the ultrasound image. The morphological image processing may include at least one of, for example, an edge detection algorithm, an image segmentation algorithm, and a machine learning algorithm.

A program for performing the above-described ultrasound diagnostic method using a computer may be recorded on a non-transitory computer-readable recording medium.

Hereinafter, detailed operations of the ultrasound diagnostic apparatus according to exemplary embodiments will be described in detail with reference to FIGS. 6 to 13. Also, hereinafter, the ultrasound diagnostic apparatus illustrated in FIG. 3 will be described as an example of the ultrasound diagnostic apparatus according to an exemplary embodiment.

Figure 6:
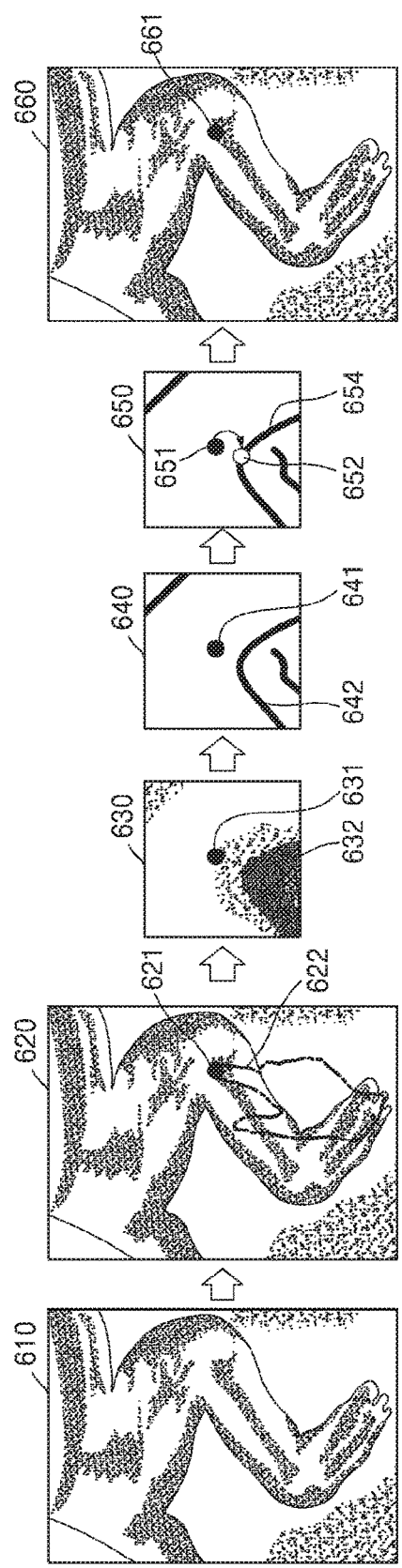
FIG. 6 is a diagram illustrating a touch point acquiring process according to an exemplary embodiment.

FIG. 6 is a diagram illustrating a touch point acquiring process according to an exemplary embodiment.

Referring to FIG. 6, the ultrasound diagnostic apparatus acquires an ultrasound image 610 of an object, based on ultrasound data. The touch interface 310 displays an ultrasound image 620 and receives at least one point on the ultrasound image 620 as a seed point 621 from the user. For example, the user may touch the touch interface 310 with a finger 622. The touch interface 310 may receive a point touched by the user as the seed point 621. The seed point 621 that is received from the user may be displayed on the ultrasound image 620. The controller 320 may acquire an image 630 of an ROI, based on the seed point 621. For example, the controller 320 may acquire a predetermined area around a seed point 631 (corresponding to the seed point 621) as the image 630 of the ROI. The image 630 of the ROI may have such a size that a portion 632 of the object may be displayed around the seed point 631. Shape information of the object may be acquired based on the image 630 of the ROI. For example, the shape information of the object may include an edge. Also, the size of the ROI may be set by the controller 320 or the user, and may be acquired by the shape information of the object. For example, when the touch interface 310 displays a leg portion of a fetus as illustrated in FIG. 6, the controller 320 may set a region represented in the image 630, which is a region having a predetermined size around the seed point 631 in the leg portion of the fetus, as the ROI. As another example, when the touch interface 310 displays an entire body of a fetus, if an object region in which the seed point 631 is recognized is determined as a leg of the fetus, based on the shape information of the object, the controller 320 may set a region including the leg of the fetus, in which the seed point is recognized, as the ROI. An acquired edge image 640 may be displayed on the display 25.

The controller 320 may use morphological image processing to acquire the shape information of the object. The morphological image processing refers to a process of morphologically analyzing an object represented in an image. For example, the morphological image processing may include a process of extracting an edge of an object represented in an image. The morphological image processing may include at least one of, for example, an edge detection algorithm, an image segmentation algorithm, and a machine learning algorithm.

The edge detection algorithm is an image processing technique that detects a feature representing a boundary of a region in an image. For example, an edge may be detected by detecting points at which the brightness of a pixel changes abruptly. Examples of the edge detection algorithm may include operator-based edge detection and Canny edge detection. Examples of an operator in the operator-based edge detection may include, but not limited thereto, a Sobel operator, a Prewitt operator, a Roberts operator, and a Laplacian operator.

The image segmentation algorithm refers to an image processing technique that divides an image into a plurality of segments. Examples of the image segmentation algorithm may include a region growing method, a split-merge method, a graphic partitioning method, and a thresholding method.

The controller 320 may acquire the touch point, based on the acquired distance between the edge and the seed point. For example, the controller 320 may automatically acquire a point 652 on an edge 642, at which the acquired distance between the edge 642 and a seed point 641 (corresponding to the seed point 621 or 631) is shortest, as a touch point. In an ultrasound image 650, the point 652, at which the acquired distance between the edge 654 and the seed point 651 is shortest, is acquired as the touch point. In this manner, according to exemplary embodiments, while the input of the user is detected by the touch interface 310 at the seed point 651, the controller 320 may correct the seed point 651 to be the touch point 652. Also, the object may be more accurately measured by using the touch point 652. Also, an ultrasound image 660 including a touch point 661 (corresponding to the touch point 652) may be displayed on the display 411.

Figure 7:
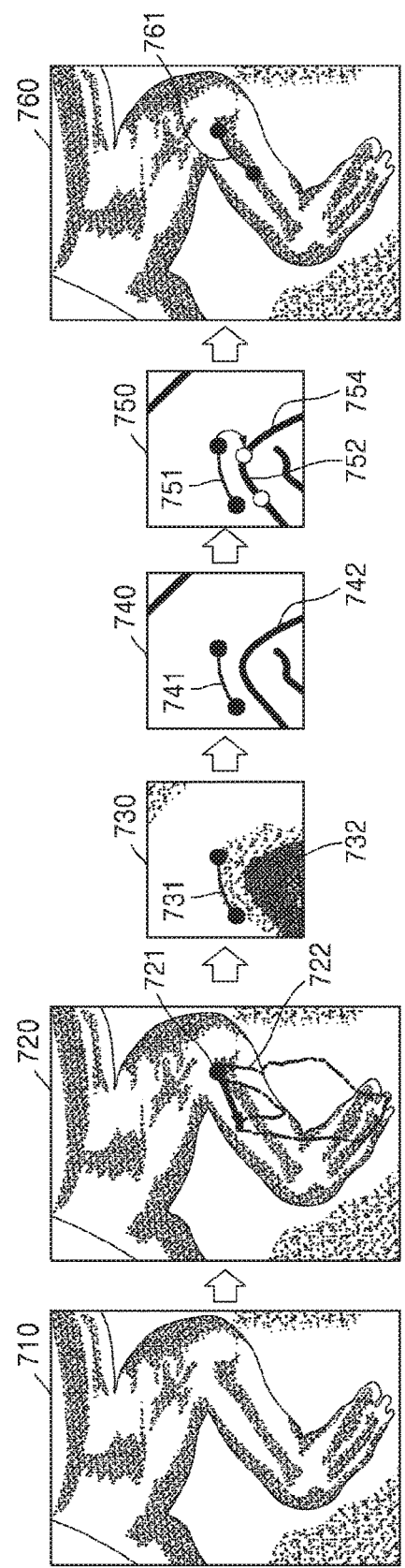
FIG. 7 is a diagram illustrating a touch line acquiring process according to an exemplary embodiment.

FIG. 7 is a diagram illustrating a touch line acquiring process according to another exemplary embodiment.

When the touch interface 310 receives a seed line including seed points from the user, the controller 320 may acquire a touch line in real time, based on the seed line.

The touch line is a line including touch points. For example, each pixel included in the touch line may be a touch point. As another example, both end points of the touch line may be touch points.

Referring to FIG. 7, the ultrasound diagnostic apparatus acquires an ultrasound image 710 of an object based on ultrasound data. The touch interface 310 receives a seed line 721 on an ultrasound image 720 from the user. For example, the user may touch the touch interface 310 with a finger 722. The seed line 721 includes seed points. For example, the touch interface 310 may acquire the seed line 721 by receiving both end points of the seed line 721 from the user. Also, the user input receiver 412 may acquire the seed line 721 including a plurality of seed points by receiving a drag of a predetermined path from the user. A drag refers to a user's action of moving the finger 722 while still touching the finger 722 to the touch interface 310. The seed line 721 received from the user may be displayed together with the ultrasound image 720.

The controller 320 may acquire an image 730 of an ROI, based on the seed line 721. For example, the controller 320 may acquire a predetermined area around a seed line 731 (corresponding to the seed line 721) as the image 730 of the ROI. The image 730 of the ROI may have such a size that a portion 732 of the object may be displayed around the seed line 731. Shape information including an edge of the object may be acquired based on the image 730 of the ROI. An edge image 740 of the object may be displayed.

The controller 320 may acquire the touch point, based on an acquired distance between the edge and the seed point. For example, the controller 320 may automatically acquire a point, at which an acquired distance between an edge 742 and a seed line 741 (corresponding to the seed line 721 or 731) is shortest, and acquire a touch line 752 based on the acquired point. For example, the controller 320 may acquire a line including a point, at which a distance between each pixel included in the seed line 741 and each pixel included in the edge 742 is shortest, as the touch line 752.

In an ultrasound image 750, a plurality of points, at which the acquired distance between the edge 754 and a corresponding point on a seed line 751 (corresponding to the seed line 741) is shortest, are acquired as the touch line 752. In this manner, according to exemplary embodiments, while the input of the user is detected by the touch interface 310 at the seed line 751, the controller 320 may determine the touch line 752 to be intended by the user. Also, the object may be more accurately measured by using the touch line 752. Also, an ultrasound image 760 including a touch line 761 (corresponding to the touch line 752) may be displayed on the display 411.

Figure 8:
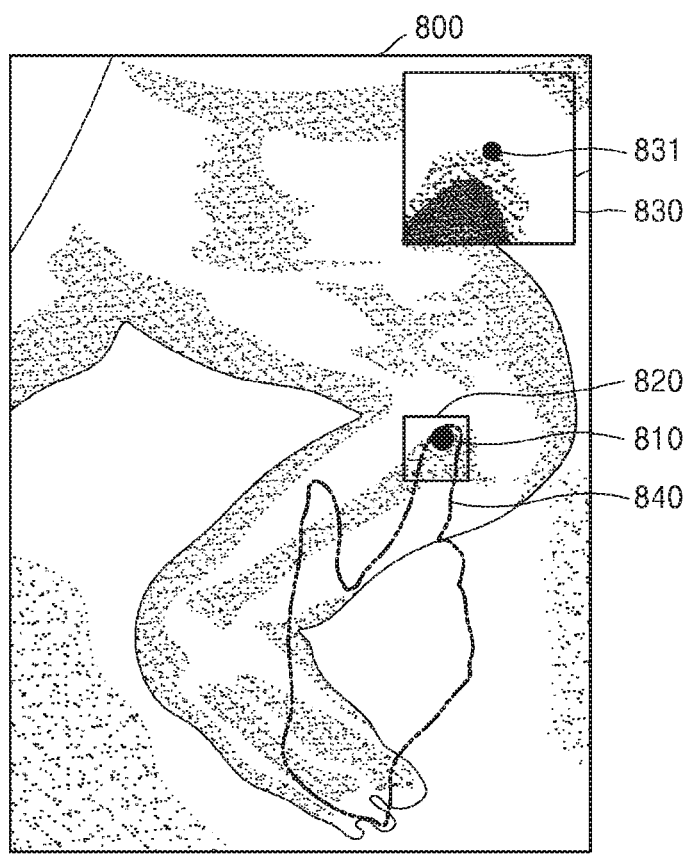
FIG. 8 is a diagram illustrating an ultrasound image according to an exemplary embodiment.

FIG. 8 is a diagram illustrating an ultrasound image according to an exemplary embodiment.

The touch interface 310 may display an image 830 of an ROI on an ultrasound image 800.

For example, the touch interface 310 may receive a seed point 810 from the user. Also, the controller 320 may acquire an ROI 820, based on the seed point 810. The image 830 of the acquired ROI may be displayed together with the ultrasound image 800. For example, the image 830 of the acquired ROI may be displayed to overlap with the ultrasound image 800, as shown in FIG. 8 or may be displayed in a separate area. Also, a seed point 831 corresponding to the seed point 810 may be displayed in the image 830 of the ROI. For example, when the user touches a point of the ultrasound image 800 with a finger 840, the touch interface 310 acquires the point at which the touch is detected as the seed point 810.

The position of the seed point 810 may be difficult to detect when the seed point 810 is hidden by the finger of the user. However, according to exemplary embodiments, when the image 830 of the ROI is displayed together with the ultrasound image 800, the user may easily detect the position of the seed point 810 through the corresponding seed point 831 on the image 830 of the ROI. The image 830 of the ROI may be an enlarged image of a portion of the ultrasound image 800. Also, the image 830 of the ROI may be an edge image (not illustrated) acquired in the ROI 820. The user may easily detect the position of the seed point 810 or 831, based on the image 830 of the ROI.

Figure 9:
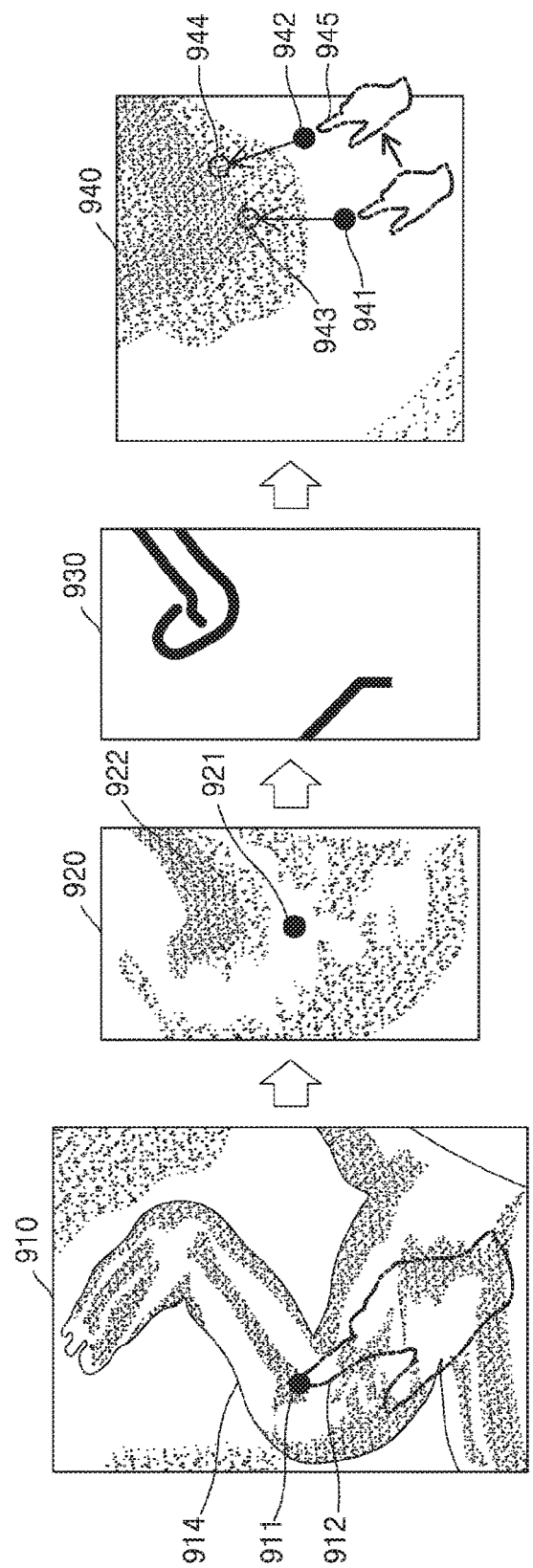
FIG. 9 is a diagram illustrating a touch point acquiring process according to an exemplary embodiment.

FIG. 9 is a diagram illustrating a touch point acquiring process according to exemplary embodiments.

Referring to FIG. 9, the touch interface 310 receives a seed point 911 on an ultrasound image 910 of an object from the user. For example, the user may touch the touch interface 310 with a finger 912. The seed point 911 received from the user may be displayed together with the ultrasound image 910. The controller 320 may acquire an image 920 of an ROI, based on the seed point 911. For example, the controller 320 may acquire a predetermined area around a seed point 921, corresponding to the seed point 911, as the image 920 of the ROI. The image 920 of the ROI may have a size such that a portion 922 of the object around the seed point 921 may be displayed. Shape information of the object may be acquired based on the image 920 of the ROI. The shape information of the object may include an edge. The display 411 may display an edge image 930 corresponding to the shape information of the object.

In an ultrasound image 940, when the user touches the touch interface 310 with a finger 945, a touch event starts, and when the user moves the finger 945 from a first point 941 to a second point 942 while still touching the touch interface 310 with the finger 945, movement of a touch point may also be displayed in real time on the display 411. The movement of the touch point may be from a third point 943 corresponding to the first point 941 and to a fourth point 944 corresponding to the second point 942. Also, when the user removes the finger 945 from the touch interface 310 at the second point 942, the touch event ends and the movement of the touch point may end at the fourth point 944. Also, the ultrasound image 940 may include at least one of the first to fourth points 941 to 944. The touch interface 310 may display in real time the ultrasound image 940 including at least one of the seed points 941 and 945, the touch points 943 and 944, and the shape information (e.g., the edge image 930) of the object. Since the user may detect a user input point in real time, the user may more clearly designate a point intended by the user.

Figure 10:
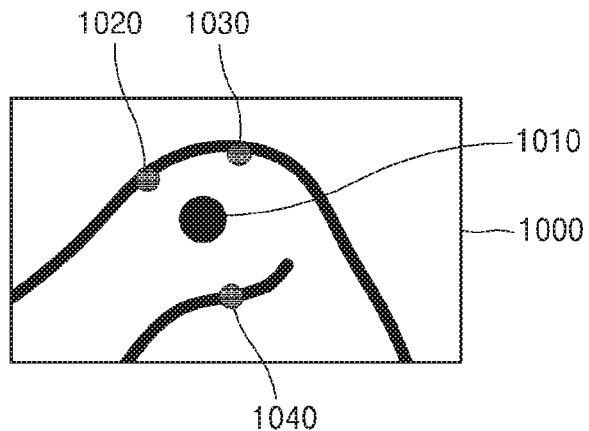
FIG. 10 is a diagram illustrating a touch point acquiring process according to an exemplary embodiment.

FIG. 10 is a diagram illustrating a touch point acquiring process according to another exemplary embodiment.

The controller 320 may acquire one or more candidate touch points, which are within a predetermined distance from the seed point, among points on the shape information of the object.

For example, when an edge image 1000 of the object is acquired based on an ultrasound image of the ROI and a seed point 1010 is received from the user, the controller 320 may acquire one or more candidate touch points 1020, 1030, and 1040 on an edge 1001 of the edge image 1000, which are within a predetermined distance from the seed point 1010. The controller 320 may automatically acquire points, which are determined to have a high probability of being touch points, as the candidate touch points 1020, 1030, and 1040, based on the seed point 1010. For example, the candidate touch points 1020, 1030, and 1040 may include a plurality of points on the edge 1001, which are at substantially the same distance from the seed point 1010. Also, the candidate touch points 1020, 1030, and 1040 may include a plurality of points on the edge 1001, which are within a predetermined distance from the seed point 1010. When a plurality of points on the edge 1001 are within a predetermined distance from the seed point 1010, the controller 320 may automatically acquire a predetermined number of candidate touch points 1020, 1030, and 1040. The edge image 1000 including at least one of the seed point 1010, the one or more points 1020 to 1040 acquired as the candidate touch points 1020 to 1040, and the edge 1001 may be displayed on the display 411. Also, the controller 320 may display an ultrasound image including the candidate touch points 1020, 1030, and 1040 so that the user may reselect any one of candidate touch points. The reselection by the user will be described below in detail with reference to FIGS. 11A and 11B.

Also, the controller 320 may detect any one of the candidate touch points 1020, 1030, and 1040 as the touch point, based on the shape information of the object. For example, the controller 320 may acquire the touch point based on a point, which is needed for diagnosing the object, based on the shape information of the object. In an exemplary embodiment illustrated in FIG. 10, for example, when the candidate touch point 1030 obtained based on the shape information of the object is needed for measuring a thigh length (FL) of a fetus, the controller 320 may determine an item (e.g., FL), which is measurable in an ROI of the object, based on the shape information of the object and acquire the touch point based on a point (e.g., the candidate touch point 1030), which is needed for measuring the determined item (FL).

Figure 11A:
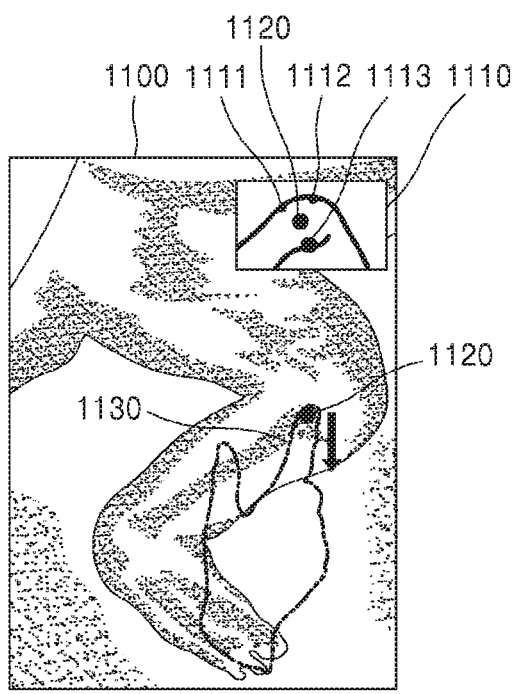
FIGS. 11A and FIG. 11B are diagrams illustrating a touch point acquiring process according to an exemplary embodiment.
Figure 11B:
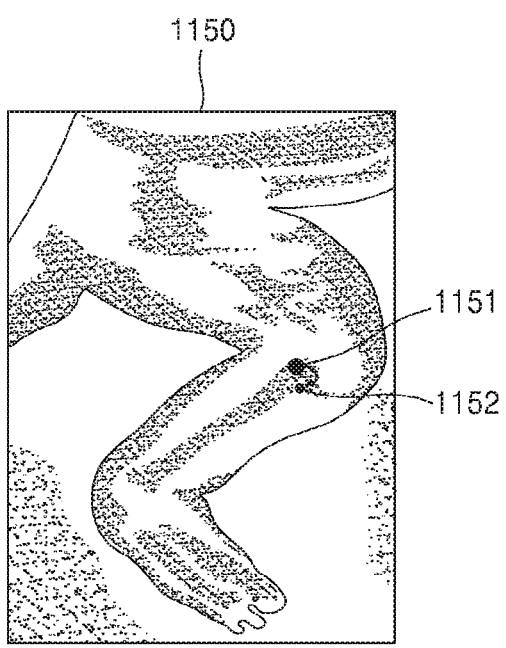

FIGS. 11A and 11B are diagrams illustrating a touch point acquiring process according to another exemplary embodiment.

The touch interface 310 may receive a predetermined motion pattern from the user, and the controller 320 may acquire one of the candidate touch points as the touch point, based on the received predetermined motion pattern.

For example, when the candidate touch points 1020, 1030, and 1040 are acquired as described with reference to FIG. 10, an ultrasound image 1100 including an edge image 1110 of an ROI may be displayed on the display 411. Also, the user may touch a finger 1130 to the touch interface 310 and the touch interface 310 may acquire a seed point 1120, at which touch by the finger 1130 is detected. Based on the acquired seed point 1120, on the edge image 1110, the controller 320 may detect a first candidate touch point 1111, a second candidate touch point 1112, and a third candidate touch point 1113 of the edge image 1110, which is displayed on the touch interface 310. The first candidate touch point 1111 is located at a top left portion of the edge image 1110. The second candidate touch point 1112 is located at the top portion of the edge image 1110 and to the right of the first candidate touch point 1111. The third candidate touch point 1113 is located at a bottom portion of the edge image 1110.

The touch interface 310 may receive a user's selection for selecting one of candidate touch points 1111, 1112, and 1113. The user's selection may be performed by using various motion patterns. The motion pattern refers to a user's action or motion performed on a touch screen. The motion pattern may include, for example, but not limited to, a length of time during which the touch screen is touched by the finger 1130, a movement path of the finger 1130 on the touch screen, and the number of times the touch interface 310 is tapped by the finger 1130.

For example, the user may use a motion pattern such as a drag for selecting one of the candidate touch points 1111, 1112, and 1113. When the user desires to select the third candidate touch point 1113, the user may drag the finger 1130 downward while touching the touch interface 310 by the finger 1130. When the touch interface 310 receives a downward drag input from the user, the third candidate touch point 1113 may be displayed differently from the first candidate touch point 1111 and the second candidate touch point 1112. For example, as illustrated in FIG. 11A, the third candidate touch point 1113 may be displayed as a larger icon than those of the first and second candidate touch points 1111 and 1112.

When the user removes the finger 1130 from the touch interface 310, a touch event ends and the third candidate touch point 1113 may be determined as a touch point 1152, as shown in FIG. 11B. Also, an ultrasound image 1150 including the determined touch point 1152 may be displayed on the display 411.

In this manner, according to exemplary embodiments, based on a seed point 1151, corresponding to the seed point 1120 or 1140, at which the input of the user through the touch interface 310 is detected, the controller 320 may acquire the touch point 1152, based on the candidate touch points 1111, 1112, and 1113. Also, the object may be more accurately measured by using the touch point 1152.

Figure 12:
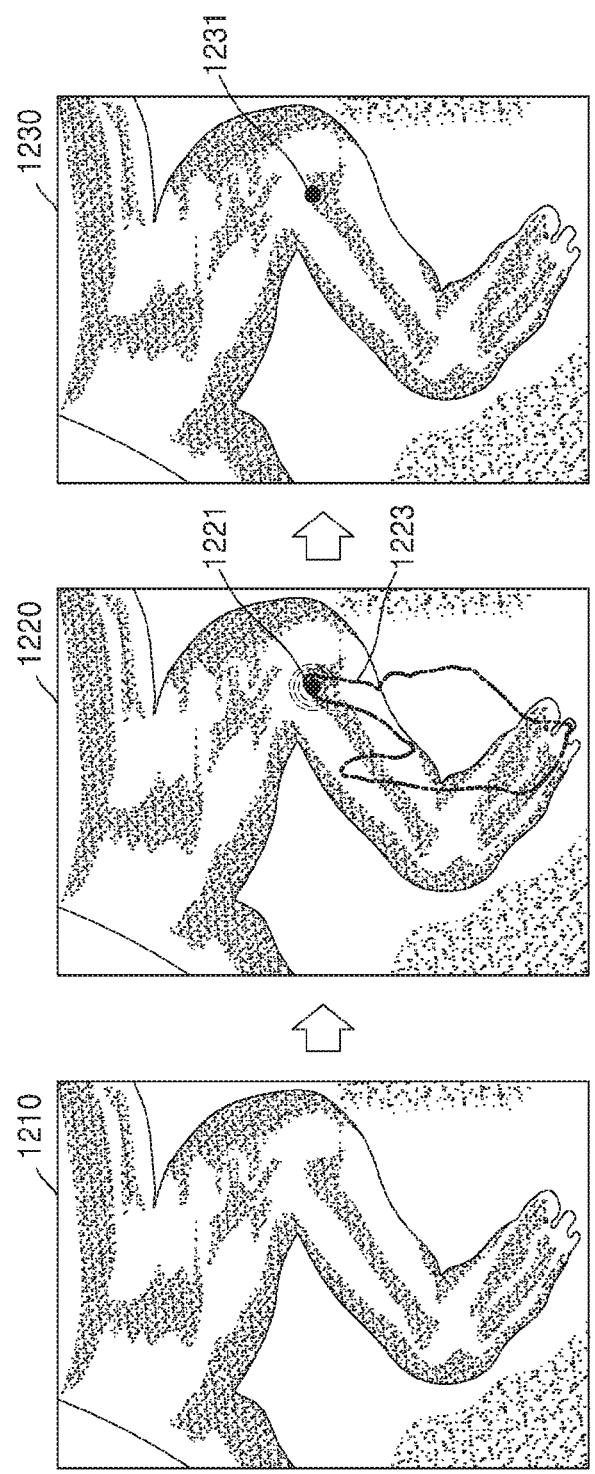
FIG. 12 is a diagram illustrating a touch point acquiring process according to an exemplary embodiment.

FIG. 12 is a diagram illustrating a touch point acquiring process according to another exemplary embodiment.

When the touch interface 310 receives a predetermined motion pattern from the user, the controller 320 may acquire the seed point as the touch point.

For example, the touch interface 310 may receive various motion patterns of the user. Also, the controller 320 may perform various operations for acquiring an input point (or seed point), based on the received various motion patterns. Referring to FIG. 12, the ultrasound diagnostic apparatus acquires an ultrasound image 1210 of an object, based on ultrasound data. The touch interface 310 receives a seed point 1221 on an ultrasound image 1220 from the user. The seed point 1221 received from the user may be displayed together with the ultrasound image 1220. In this case, for example, the user may touch a touch screen of the touch interface 310 with a finger 1223 for a predetermined time or more. The touch interface 310 may receive a motion pattern, which corresponds to a long touch for a predetermined time or more, from the user. The controller 320 may acquire the seed point 1221 as a touch point 1231, based on the motion pattern without acquiring shape information of the object (e.g., an edge image). An ultrasound image 1230 including the acquired touch point 1231 may be displayed on the display 411.

Figure 13A:
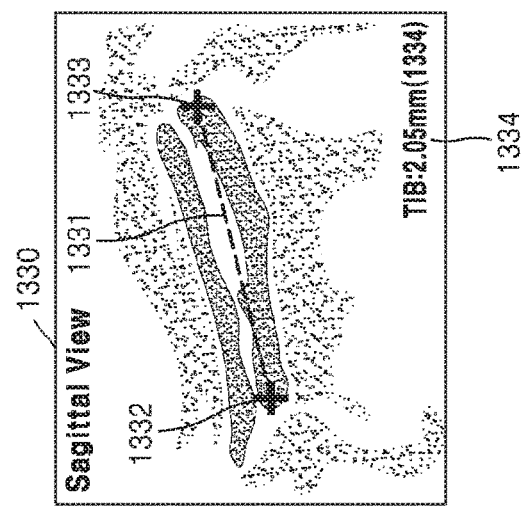
FIGS. 13A, 13B, and 13C are diagrams illustrating measurements based on a touch point acquired according to an exemplary embodiment.
Figure 13B:
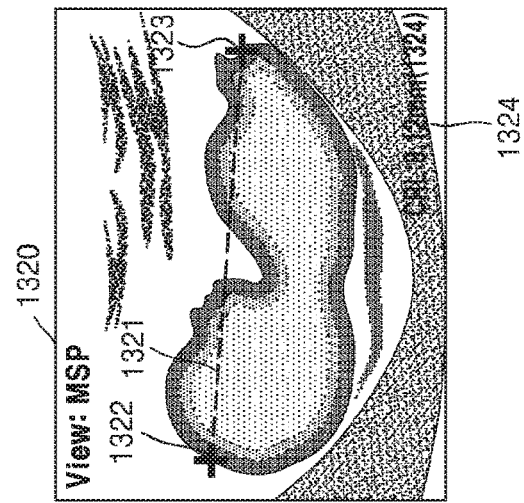
Figure 13C:
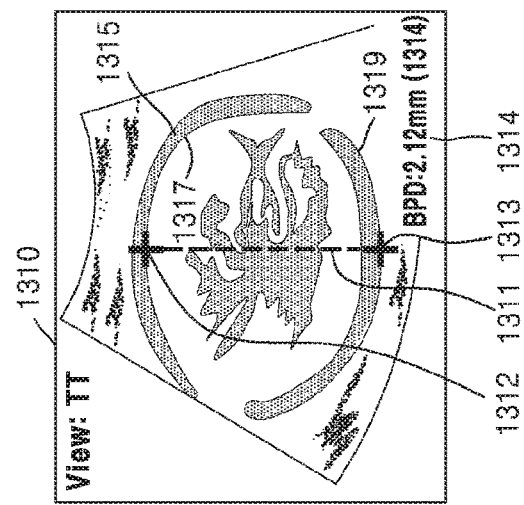

FIGS. 13A, 13B, and 13C are diagrams illustrating measurements based on a touch point acquired according to an exemplary embodiment.

FIG. 13A shows an ultrasound image 1310, which is an ultrasound image of a head portion of a fetus. A caliper 1311 includes points 1312 and 1313 at both ends. The touch interface 310 may acquire the points 1312 and 1313 of the caliper 1311 by receiving a touch from the user.

In this regard, measurement information may vary according to the positions of the points 1312 and 1313 included in the caliper 1311. For example, when a point located outside a skull image 1315 of the object at one side and another point located inside the skull image 1315 at an opposite side are received by the touch input from the user, the measurement information may be information about a caliper for measuring a biparietal diameter (BPD). Also, when a point located outside the skull image 1315 of the object at one side and another point located outside the skull image 1315 at an opposite side are received by the touch input from the user, the measurement information may be information about a caliper for measuring a head circumference (HC). The HC may be acquired based on the measurement information. Thus, the measurement information may be acquired differently according to the positions of the points received by the touch input of the user.

When the user desires to measure the BPD, the user may touch the point 1312 located inside the skull image 1315 of the object at one side and the point 1313 located outside the skull image 1315 of the object at an opposite side. In this regard, the ultrasound diagnostic apparatus according to exemplary embodiments may accurately determine the touch point, based on the seed point (e.g., the points 1312 and 1313) received by the touch interface 310 even when the skull image 1315 of the object on the ultrasound image 1310 is relatively thin. That is, even when the skull image 1315 of the object on the ultrasound image 1310 is relatively thin and thus the touch interface 310 receives a point near the point 1312 as the seed point, the controller 320 may acquire the point 1312 as the touch point, based on the seed point. Also, even when the touch interface 310 receives a point near the point 1313 as the seed point, the controller 320 may acquire the point 1313 as the touch point, based on the seed point. For example, the controller 320 may determine the point 1312 or 1313 as the touch point based on the seed point near the point 1312 or 1313 when the seed point is within a threshold distance from the point 1312 or 1313.

The configurations described with reference to FIGS. 3 to 12 may be used to acquire an accurate touch point. For example, as described with reference to FIGS. 11A and 11B, the controller 320 may acquire candidate touch points respectively positioned inside and outside the skull image 1315 of the object on the ultrasound image 1310 and acquire the points 1312 and 1313 as the touch points, based on the selection received from the user.

Since the point 1312 is located on an inner side (or an inner surface 1317) of the skull image 1315 of the object at one side on the ultrasound image 1310 and the point 1313 is located on an outer side (or an outer surface 1319) of the skull image 1315 of the object at an opposite side on the ultrasound image 1310, the BPD may be acquired by using the caliper 1311 including the points 1312 and 1313. A measurement value 1314 of the BPD acquired by using the caliper 1311 may be about 2.12 mm.

FIG. 13B shows an ultrasound image 1320, which is an ultrasound image of a fetus. Also, the ultrasound image 1320 is captured on a mid-sagittal plane (MSP). A caliper 1321 includes points 1322 and 1323 at both ends. The touch interface 310 may acquire the points 1322 and 1323 of the caliper 1321 by receiving a touch from the user. For example, the touch interface 310 may acquire the points 1322 and 1323 of the caliper 1331 using various methods described above. A crown rump length (CRL) may be acquired by using the caliper 1321 including the points 1322 and 1323. A measurement value 1324 of the CRL acquired by using the caliper 1321 may be about 8.12 mm.

FIG. 13C shows an ultrasound image 1330 is an ultrasound image of a fetus. A caliper 1331 includes points 1332 and 1333 at both ends. The touch interface 310 may acquire the points 1332 and 1333 of the caliper 1331 by receiving a touch from the user. For example, the touch interface 310 may acquire the points 1332 and 1333 of the caliper 1331 using methods described above. A Tibia (TIB) may be acquired by using the caliper 1331 including the points 1332 and 1333. A measurement value 1334 of the TIB acquired by using the caliper 1331 may be about 2.05 mm.

As described above, according to the exemplary embodiments, the user may more accurately input a desired point on the ultrasound image by using the touch-based user interface.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An ultrasound diagnostic apparatus comprising:
a touch interface configured to display an ultrasound image of an object, and receive a user touch on the ultrasound image; and
a controller configured to acquire a first point, at which the user touch is sensed, acquire shape information of the object, and perform a control to display, on the ultrasound image, a second point corresponding to the user touch, the second point being determined based on the first point and the shape information,
wherein the controller is configured to determine the second point based on a distance between the first point and a point of the object, the point of the object being determined based on the shape information.

2. The ultrasound diagnostic apparatus of claim 1, wherein the controller is configured to acquire the shape information comprising information about an edge of the object, based on the ultrasound image, acquire distances between the first point and points on the edge, and determine the second point, based on the distances between the first point and the points on the edge.

3. The ultrasound diagnostic apparatus of claim 1, wherein the controller is configured to acquire a region of interest (ROI) of a portion of the ultrasound image, based on the first point, and acquire the shape information of the object by image processing the ROI.

4. The ultrasound diagnostic apparatus of claim 3, wherein the touch interface is configured to display an enlarged image of the ROI on the ultrasound image.

5. The ultrasound diagnostic apparatus of claim 1, wherein, when the touch interface receives a first line comprising first points obtained from the user touch, the controller is configured to determine a second line comprising second points corresponding to the user touch in real time, based on the first line.

6. The ultrasound diagnostic apparatus of claim 1, wherein
the shape information of the object comprises information about an edge of the object, and
the controller is configured to automatically determine a point, which is closest to the first point, among points on the edge, as the second point.

7. The ultrasound diagnostic apparatus of claim 1, wherein
the shape information of the object comprises information about an edge of the object, and
the controller is configured to determine one or more candidate second points, which are within a certain distance from the first point, among points on the edge.

8. The ultrasound diagnostic apparatus of claim 7, wherein
the touch interface is configured to receive a motion pattern from a user, and
the controller is configured to determine one of the one or more candidate second points as the second point, based on the received motion pattern.

9. The ultrasound diagnostic apparatus of claim 1, wherein the controller is configured to acquire the shape information of the object by morphological image processing.

10. The ultrasound diagnostic apparatus of claim 9, wherein the morphological image processing comprises at least one of an edge detection algorithm, an image segmentation algorithm, and a machine learning algorithm.

11. An ultrasound diagnostic method comprising:
receiving a user touch on an ultrasound image of an object;
acquiring a first point, at which the user touch is sensed;
acquiring shape information of the object;
determining a second point corresponding to the user touch, based on the first point and the shape information; and
displaying the second point together with the ultrasound image,
wherein the determining the second point comprises determining the second point based on a distance between the first point and a point of the object, the point of the object being determined based on the shape information.

12. The ultrasound diagnostic method of claim 11, wherein
the acquiring the shape information of the object comprises acquiring the shape information comprising information about an edge of the object, based on the ultrasound image, and
the determining the second point comprises:
acquiring distances between the first point and points on the edge; and
determining the second point, based on the distances between the first point and the points on the edge.

13. The ultrasound diagnostic method of claim 11, wherein the acquiring the shape information of the object comprises:
acquiring a region of interest (ROI) of a portion of the ultrasound image, based on the first point; and
acquiring the shape information of the object by image processing the ROI.

14. The ultrasound diagnostic method of claim 13, wherein the displaying the second point comprises displaying an enlarged image of the ROI on the ultrasound image.

15. The ultrasound diagnostic method of claim 11, wherein
the acquiring the first point comprises receiving a first line comprising first points obtained from the user touch, and
the determining the second point comprises determining a second line comprising second points corresponding to the user touch in real time, based on the first line.

16. The ultrasound diagnostic method of claim 11, wherein
the shape information of the object comprises information about an edge of the object, and
the determining the second point comprises automatically determining a point, which is closest to the first point, among points on the edge, as the second point.

17. The ultrasound diagnostic method of claim 11, wherein
the shape information of the object comprises information about an edge of the object, and
the determining the second point comprises determining one or more candidate second points, which are within a certain distance from the first point, among points on the edge.

18. The ultrasound diagnostic method of claim 17, wherein
the receiving the user touch comprises receiving a motion pattern from a user, and
the determining the second point comprises determining one of the one or more candidate second points as the second point, based on the received motion pattern.

19. The ultrasound diagnostic method of claim 11, wherein the acquiring the shape information of the object comprises acquiring the shape information of the object by morphological image processing.

20. A non-transitory computer-readable recording medium that stores a program comprising program instructions which, when executed by a computer, cause the computer to perform an ultrasound diagnostic method comprising:
receiving a user touch on an ultrasound image of an object;
acquiring a first point, at which the user touch is sensed;
acquiring shape information of the object;
determining a second point corresponding to the user touch, based on the first point and the shape information; and
displaying the second point together with the ultrasound image,
wherein the determining the second point comprises determining the second point based on a distance between the first point and a point of the object, the point of the object being determined based on the shape information.

* * * * *